United States Patent
Zenge

(10) Patent No.: US 9,782,106 B2
(45) Date of Patent: Oct. 10, 2017

(54) METHOD AND MAGNETIC RESONANCE APPARATUS FOR DETERMINATION OF MAGNETIC RESONANCE ANGIOGRAPHY IMAGES USING TIME-OF-FLIGHT ANGIOGRAPHY

(71) Applicant: Siemens Aktiengesellschaft, Munich (DE)

(72) Inventor: Michael Zenge, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 13 days.

(21) Appl. No.: 14/967,840

(22) Filed: Dec. 14, 2015

(65) Prior Publication Data
US 2016/0166172 A1    Jun. 16, 2016

(30) Foreign Application Priority Data
Dec. 15, 2014 (DE) .................. 10 2014 225 846

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/7246* (2013.01); *A61B 5/7289* (2013.01);
(Continued)

(58) Field of Classification Search
CPC   G06T 7/0012; G06T 7/38; G06T 7/32; G06T 2207/30101; G06T 2207/30104;
(Continued)

(56) References Cited

U.S. PATENT DOCUMENTS 5,859,922 A * 1/1999 Hoffmann .............. A61B 6/584
                                                           382/128
6,023,635 A * 2/2000 Liu ..................... G01R 33/4835
                                                           324/307
(Continued)

OTHER PUBLICATIONS

McCauley, Thomas R., Ahmed Monib, Kevin W. Dickey, John Clemett, G. H. Meier, T. K. Egglin, R. J. Gusberg, M. Rosenblatt, and J. S. Pollak. "Peripheral vascular occlusive disease: accuracy and reliability of time-of-flight MR angiography." Radiology 192, No. 2 (1994): 351-357.*

(Continued)

*Primary Examiner* — Sumati Lefkowitz
*Assistant Examiner* — Carol Wang
(74) *Attorney, Agent, or Firm* — Schiff Hardin LLP

(57) ABSTRACT

In a method and apparatus, magnetic resonance angiography images of an examination volume of a patient are obtained using time-of-flight angiography in a magnetic resonance scanner. By continuous recording, a number of two-dimensional slice images covering the examination volume along an axial direction are acquired in a slice-by-slice layer-wise, such as with overlapping. The slice images are divided into groups of, in each case, a predetermined number of consecutive slice images in the axial direction. A maximum intensity projection image is determined for each group, and the angiography images are determined as the maximum intensity projection images and/or dependent on the maximum intensity projection images.

17 Claims, 2 Drawing Sheets

(51) Int. Cl.
*G06T 11/00* (2006.01)
*G01R 33/563* (2006.01)

(52) U.S. Cl.
CPC ........ *G01R 33/5635* (2013.01); *G06T 11/008* (2013.01); *G01R 33/56383* (2013.01); *G06T 2211/404* (2013.01); *G06T 2211/424* (2013.01)

(58) Field of Classification Search
CPC . G06T 2207/30004; G06T 2207/10088; G06T 2207/30048; G06T 2207/30016; G06T 2207/30096; G06T 2207/10016; G06T 2207/20108; G06T 2207/30196; G06T 11/008; G06T 2211/404; G06T 2211/424; G01R 33/5635; G01R 33/4835; G01R 33/56383; A61B 2090/364; A61B 2090/374; A61B 5/055; A61B 5/7289; A61B 5/7246; A61B 5/489; A61B 6/504; A61B 6/5264; A61B 2576/00; A61B 2017/00699; A61B 8/0891

See application file for complete search history.

(56) References Cited

U.S. PATENT DOCUMENTS

| | | | |
|---|---|---|---|
| 6,043,655 A | 3/2000 | Makita et al. | |
| 6,377,835 B1* | 4/2002 | Schoenberg | A61B 5/055 324/306 |
| 6,505,064 B1* | 1/2003 | Liu | G06T 11/206 324/307 |
| 6,760,611 B1* | 7/2004 | Watanabe | G01R 33/5601 324/307 |
| 7,031,504 B1* | 4/2006 | Argiro | A61B 6/504 382/131 |
| 2003/0016851 A1* | 1/2003 | Kaufman | A61B 6/5264 382/131 |
| 2005/0111720 A1* | 5/2005 | Gurcan | G06T 7/0012 382/131 |
| 2008/0119721 A1* | 5/2008 | Kimura | A61B 5/055 600/410 |
| 2008/0262346 A1* | 10/2008 | Assis | A61B 6/507 600/431 |
| 2009/0219021 A1 | 9/2009 | Dai et al. | |
| 2010/0128952 A1* | 5/2010 | Schmitt | A61B 5/02007 382/131 |
| 2011/0142288 A1* | 6/2011 | Diamant | G06T 7/0016 382/107 |
| 2011/0263970 A1* | 10/2011 | Xu | A61B 5/055 600/419 |
| 2012/0226141 A1* | 9/2012 | Shinoda | G01R 33/48 600/419 |
| 2012/0245453 A1* | 9/2012 | Tryggestad | A61B 6/463 600/413 |
| 2012/0271156 A1* | 10/2012 | Bi | A61B 5/055 600/415 |
| 2013/0119983 A1 | 5/2013 | Zenge | |
| 2013/0190633 A1* | 7/2013 | Dorando | A61B 5/02158 600/486 |
| 2014/0270437 A1* | 9/2014 | Shreiber | A61B 6/481 382/130 |
| 2015/0080731 A1* | 3/2015 | Yamamoto | A61B 8/5207 600/447 |
| 2016/0012613 A1* | 1/2016 | Okerlund | G06T 11/003 382/131 |
| 2016/0018501 A1* | 1/2016 | Kimura | A61B 5/055 324/322 |

OTHER PUBLICATIONS

Baumann, : "Time-of-flight-Magnetresonanzangiographie mit kontinuierlich bewegtem Patiententisch"; Inaugural Dissertation zur Erlangung des Doktorgrades der Fakultät für Mathematik and Physik der Albert-Ludwigs-Universiät Freiburg im Breisgau, (2011).

Baumann, et. al.: "Peripheral Vessel Scout Imaging Based on Continuously Moving Table Acquisition of Projection Data", J Comput Assist Tomogr vol. 36, No. 5, pp. 591-595, (2012).

* cited by examiner

METHOD AND MAGNETIC RESONANCE APPARATUS FOR DETERMINATION OF MAGNETIC RESONANCE ANGIOGRAPHY IMAGES USING TIME-OF-FLIGHT ANGIOGRAPHY

BACKGROUND OF THE INVENTION

Field of the Invention

The invention concerns a method for creating magnetic resonance angiography images of an examination volume of a patient using time-of-flight angiography in a magnetic resonance apparatus wherein, by continuous recording, a number of two-dimensional slice images covering the examination volume along an axial direction are acquired slice-by-slice, particularly in an overlapping manner. The invention also concerns a magnetic resonance apparatus and a non-transitory, computer-readable data storage medium encoded with programming instructions computer program to implement such a method.

Description of the Prior Art

Magnetic resonance imaging is a known modality for creating magnetic resonance angiography images. Two fundamentally different approaches exist for that purpose. In a first approach, prior to creating the magnetic resonance images, a contrast agent is injected into a subject with which the vessels in which the contrast agent flow being clearly highlighted thereby. Because the administration of contrast agent in modern medical imaging is preferred to be avoided as much as possible, procedures are also proposed in which it is possible to dispense with injecting a contrast agent (frequently referred to as "non-contrast MR angiography"). The best-known example of this is known as time-of-flight angiography with a magnetic resonance apparatus. This exploits the fact that after a saturation of spins is achieved in one slice, "fresh" blood that flows into this slice, and which has not experienced the high frequency pulses resulting in the saturation, has a significantly higher signal intensity. Ideally only the signal of blood that is flowing into the slice is measured.

It is particularly advantageous here for the measurement to take place in the arterial phase, since arterial blood is pumped through the arteries in a pulsatile manner. The arterial phase is understood to mean the phase of the cardiac cycle in which the heart pumps the blood into the arteries. By contrast, the venous phase is the phase of the cardiac cycle in which the blood is fed back via the veins to the heart. In the arterial phase, blood with non-saturated spins therefore quickly penetrates the vessels in the examination volume, so that these can be seen particularly clearly.

It was therefore proposed to perform the recording (acquisition) of the magnetic resonance angiography images in a triggered manner, in particular on the basis of an EKG (electrocardiogram). In this way the arterial phase can be identified chronologically so that the measurement then ideally takes place when blood with non-saturated spins flows through the blood vessels in the examination volume in large quantities. When EKG signals are used to trigger the time-of-flight magnetic resonance angiography, a series of disadvantages nevertheless exists. Couplings of the radio-frequency signals generated by the magnetic resonance scanner into the EKG device are possible, and may result in incorrect actuation signals on the part of the EKG device. A further problem occurs when the patient has a variable heartbeat (arrhythmia), since problems can then occur during data acquisition, particularly when the data acquisition requires determining the phase. A delay time must be planned as precisely as possible, since the further the blood vessels to be examined are from the heart, the longer the blood needs in order actually to enter into the examination volume. These delay times are often extremely difficult to estimate. Finally, EKG actuation signals and the corresponding arterial or venous phase at distal segments of a hemo-vascular tree only have minor correlations, so that the EKG actuation signals, especially with existing standard deviations in the physiology of the patient, to which the examination applies if necessary, do not conform optimally to the respective phases.

US 2013/0119983 A1 proposes a method for generating angiography images, which can determine angiography images, in particular angiography images of the arterial phase, without using an EKG device or a trigger signal. It is proposed to divide the magnetic resonance data in k-space into different groups in respect of the cardiac cycle, by a Fourier transformation of the detected magnetic resonance data being performed in the temporal respect in order to generate a frequency spectrum of the magnetic resonance data. A corresponding analysis of the frequency spectrum, in particular of the temporal course of the averaged energy from detected radii during radial scanning of k-space, allows the arterial phase to be differentiated from the venous phase and magnetic resonance angiography images in the position space can be generated from the magnetic resonance data of the arterial phase. This analysis is relatively complicated and not always completely reliable.

SUMMARY OF THE INVENTION

An object of the invention is to provide an improved method compared with the above-described conventional techniques, which can be performed as a post-processing step in the spatial domain.

In order to achieve this object, in accordance with the invention in a method of the type cited above, the slice images are divided into groups of, in each case, a predetermined number of consecutive slice images in the axial direction, and a maximum intensity projection image is determined for each group and diagnostic angiography images are determined respectively as the maximum intensity projection images of each group or are determined dependent on these maximum intensity projection images.

Modern imaging methods are used to allow slice images to be recorded with a time interval that is shorter than a conventional cardiac phase. This means that the image recording rate of the slice images is greater than the heart rate. Fundamentally known, rapid magnetic resonance imaging methods, such as those using a radial scanning of k-space or a Cartesian scanning of k-space, in order to then perform an iterative image reconstruction, can be used so that a time-of-flight angiography at rates of for instance 10 slice images per second and more is conceivable. A series of slice images, which cover at least one cardiac cycle chronologically, particularly in groups in each case, is consequently produced.

Further consideration is now made of the fact that the strongest measured signal in time-of-flight angiography arises from the arterial phase, in which pulsatile, fresh blood penetrates into the blood vessels of the slice mapped by the slice image, in which fresh blood no saturation exists so that it is consequently clearly visible. Particularly high signal values in the slice images are thus only to be expected in the arterial phase, particularly if on account of the expected blood flow direction, as essentially known, further saturation regions are set in the direction from which the venous backflow is expected. In accordance with the invention, as noted above, the slice images, which essentially chronologically cover a complete cardiac cycle, are divided into groups, and it is assumed that ideally only one of these images, namely the one that was recorded during the pulsatile influx of fresh blood, indicates strong signals. If a maximum intensity projection image (MIP="maximum intensity projection") is now foil led across a stack of the predetermined number of slice images recorded chronologically immediately after one another, the contrast of the arterial peak is collected in a single image. With the maximum intensity projection, the image value (of the already reconstructed slice image in the spatial domain) is consequently selected across all images in the group, this image value indicating the highest magnetic resonance signal, consequently (regardless of noise effects) originating from the arterial phase, in which fresh blood flows in a pulsatile manner into the blood vessels.

Within the scope of the present invention, the slice images for determining the maximum intensity projection image, as already mentioned, are evaluated in the spatial domain. This means that this is a post-processing step, since the slice images were reconstructed. The slice images can be recorded here, as was described for instance in US 2013/0119983 A1 cited in the introduction, by gradient echo sequences, specifically with a FLASH recording technique ("Fast Low Angle Shot"), or a TrueFISP technique ("True Fast Imaging with Steady State Precession") for instance. The reconstruction of the slice images in the spatial domain can take place in a conventional manner, preferably with the use of an iterative reconstruction method, wherein missing or not detected magnetic resonance data are supplemented by previous knowledge relating to the slice image to be created. This can involve the position and/or the dimensions of blood vessels in the volume segment to be detected for instance. Deviations from a position of this type detected once or dimensions detected once can be taken into account during the iterative reconstruction for instance on account of a corresponding penalty. In particular, it is consequently possible to use compressed sensing in advance as a variant of the iterative reconstruction method, in which this is a statistical technique for data acquisition and data estimation, which aims at detecting or sensing only comparably few measurement points in k-space. Under certain conditions, magnetic resonance data of this type detected sparsely in k-space can reproduce virtually the entire information.

Since the slice images are naturally assigned in each case to respectively different recording positions along the axial direction, in order to obtain a stack of overlapping slice images, which cover the examination volume along the axial direction, the position of this type along the axial direction must naturally also be assigned to the angiography images. It is possible for the maximum intensity projection images themselves to be determined as the angiography images, to which a recording position is then naturally also to be assigned, in order to be able to spatially arrange them for instance if a three-dimensional data record or a three-dimensional representation is to take place. It is naturally possible here to use an average recording position of the slice images of the group, from which the maximum intensity projection image originated. In this respect, the invention nevertheless provides improvement possibilities in two respects. Improvement is achieved with respect to determining the angiography images themselves, since the maximum intensity projection images could be noise-amplified by forming the maximum intensity projection. Improvement is also achieved with respect to determining the position to be used of the angiography image along the axial direction.

To this end, in a preferred embodiment of the invention, a correlation measure is determined for all slice images of the group with respect to the maximum intensity projection image. This correlation measure can be used advantageously in two ways. In a particularly advantageous embodiment, provision can be made for the slice image with the highest correlation measure and/or all slice images, the correlation measure of which exceeds a threshold value for the correlation measure, to be used as an angiography image. In this case, the maximum intensity projection images are therefore not used as angiography images since these could be loaded with a stronger noise and in respect of the recording position cannot be assigned sufficiently accurately, but instead the maximum intensity projection images are used as a type of reference image, with respect to which the correlation of the slice images of the group is determined as a correlation measure. If an extremely high correlation measure exists, it is assumed that the corresponding slice image is the slice that has the strongest magnetic resonance signals, consequently the arterial influx, from which the majority of image values were consequently taken over into the maximum intensity projection image. The predetermined number of consecutive slice images in the axial direction can ideally be selected such that one cardiac cycle is always detected, consequently also only one of the slice images actually shows the pulsatile flow of blood in the arterial phase. It may thus naturally occur in practice, as detailed below, that two slice images showing arterially inflowing blood are contained in one group. It is then conceivable to only use the slice image with the highest correlation measure. It may, however, also be expedient, in the case of several slice images with a high correlation measure, in particular a correlation measure exceeding a threshold value, to evaluate all these slice images as an angiography image. Regardless of the precise procedure, slice images, as has been explained, are naturally already assigned recording positions so that they can be spatially assigned without problems within the existing angiography image data record.

Another embodiment is particularly suitable if a high image recording rate was selected, wherein the pulsatile influx of blood in the arterial phase is detected by a number of images, consequently already expediently combined in the maximum intensity projection image, so as to use the correlation measure to position this in a spatially accurate manner. In this embodiment, a recording position assigned to the slice image with the highest correlation measure, is assigned to the maximum intensity projection image as an angiography image. The highest correlation measure indicates the slice images from which the majority of image values of the maximum intensity projection image originate, and is also used expediently to locate the maximum intensity projection image correctly.

As already explained, it is particularly expedient for the predetermined number to be determined as a function of the image recording rate of the slice images and a duration of a cardiac cycle, in particular as the duration multiplied by the image recording rate. A group then essentially covers a cardiac cycle, but should in most instances include an influx of fresh blood in the arterial phase in a mostly fairly accurate manner. Due to the simple realization, it is inventively preferred for a predetermined maximum duration of a cardiac cycle to be used as the duration, in particular in the range of 800 to 1100 ms, preferably 1000 ms. Longer durations are expediently assumed here in order in each case to comprise at least one influx of blood in the arterial phase in one group, in order to avoid "dark" angiography images, which were produced from a group in which the pulsatile influx over time into the volume segments mapped by the slice images of the group were not contained. 1000 ms is therefore preferably used as a default, which would correspond to a rather long duration of a cardiac cycle, which in most cases already provides suitable and useful results.

Alternatively, it is also possible to use a patient-specific duration of the cardiac cycle as the duration. It is possible to detect the duration of the cardiac cycle of a specific patient by measurement with further measuring devices in addition to the magnetic resonance scanner, for instance by using an EKG, but this is less preferable for the reasons cited above. Consequently, it is preferred to determine a patient-specific duration of the cardiac cycle with the magnetic resonance scanner, wherein navigator measurements and the like for instance, which are upstream of the recording of the slice images. Preferably, however, a patient-specific duration of the cardiac cycle is determined by evaluating the slice images. Since strong magnetic resonance signals, as explained, always ultimately occur in the arterial phase during the pulsatile inflow of the blood, it is possible also to estimate the duration of the cardiac cycle by analyzing slice images. For instance, signal frequencies can be analyzed in the series of slice images and/or slice images with a certain signal content can be sought and their intervals evaluated. Other possibilities are also conceivable. In order to keep the method simple, it is preferred to estimate the predetermined maximum duration of a cardiac cycle as the duration of the cardiac cycle.

As already mentioned, all slice images are preferably displaced with respect to each other. Theoretically this can take place by displacing the volume segment to be mapped by the slice image in space, but it is more preferable to determine the slice images in a spatially constant slice position, by a continuously moving patient table or bed with the patient thereon. In this way, the patient is moved slowly through the slice during the data acquisition, so that each slice image shows a volume segment displaced slightly in the axial direction, which is then the direction of movement of the patient bed.

In a preferred embodiment of the invention, the movement speed of the patient bed is selected such that the patient bed is moved by one slice thickness during the acquisition of the predetermined number of images. In this way, slices that essentially adjoin one another are provided as angiography images, these slices covering the examination volume with as little overlap as possible. If ten slice images per second are recorded with a slice thickness of 3 mm for instance, and a duration of the cardiac cycle of 1000 ms is further assumed, and 10 is consequently selected as a predetermined number of slices per second, it has proven expedient to adjust the speed of the patient bed such that the patient was moved 0.3 mm further between the acquisition of two successive slice images. Each group of slice images in this way covers one slice thickness, so that the overlap is minimized while still retaining good coverage. If a three-dimensional representation is desired, interpolation methods and similar techniques can be used if gaps exist between the individual angiography images.

It should be noted here that it is also possible to obtain angiography images that overlap (when possible) into account in a targeted manner, and consequently to use a smaller patient bed movement increment for instance, but a longer measurement time must then be expected.

It should be noted again that components from the venous phase, if the blood flows back relatively uniformly through the slice mapped by a slice image, can avoid developing signal components, by, as usual, a saturation region being used in the corresponding direction. If an image is viewed in the leg region for instance, the flow direction of the arterial blood is directed downwardly, in other words toward the feet, while the venous blood flows back again to the heart. If a saturation region is then used on the foot side, the blood of the venous backflow in the venous phase does not deliver any signal components which may be relevant to the maximum intensity projection.

The invention also encompasses a magnetic resonance apparatus, having a control computer designed to perform the inventive method. This means that the inventive post-processing step for selecting or determining angiography images from the slice images can be provided directly at the magnetic resonance scanner of the apparatus. The control computer thus has processors or modules, in order to actuate the components of the magnetic resonance scanner to record the magnetic resonance data of the slice images. The computer also includes a reconstruction processor for reconstructing the slice images in the spatial domain from the magnetic resonance data, and a post-processing module or processor for the final determination of the magnetic resonance angiography images. All embodiments relating to the inventive method can be implemented by the inventive magnetic resonance apparatus, so that the cited advantages can also be achieved therewith.

The invention also encompasses a non-transitory, computer-readable data storage medium encoded with programming instructions that cause a computer to operate a magnetic resonance apparatus to perform the steps of the inventive method, when the storage medium is loaded in the computer. The storage medium may be a CD-ROM, for example.

The present invention therefore enables the realization of time-of-flight magnetic resonance angiography in real-time with adequate background suppression. Slice images can be recorded for instance with rapid gradient echo sequences using radial or Cartesian scanning, while a patient bed is continuously moved so that a stack of two-dimensional slice images is produced with a considerable overlap between the individual slices. A retrospective gating is then performed in the position space, by techniques of maximum intensity projection (MIP) being used in any case. In particularly preferred exemplary embodiments, further improvements are achieved by considering the cross-correlation between the maximum intensity projection image and the original input images, in other words the slice images of the group. In this way, the angiography images showing the arterial phase can either be selected from the original slice images, or else it is also conceivable to use the maximum intensity projection images as angiography images.

DESCRIPTION OF THE PREFERRED EMBODIMENTS

Figure 1:
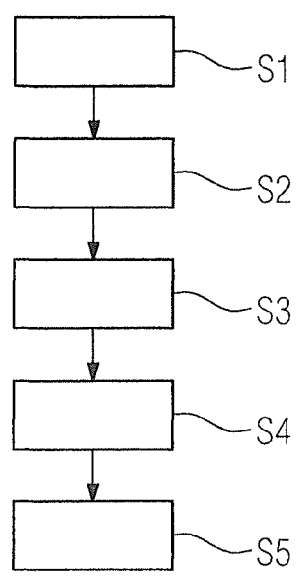
FIG. 1 is a flowchart of an exemplary embodiment of the inventive method.

FIG. 1 shows a flowchart of an exemplary embodiment of the inventive method for determining magnetic resonance angiography images of time-of-flight magnetic resonance angiography. Magnetic resonance data in an examination volume are recorded in step S1 with a magnetic resonance scanner, the data relating to significantly overlapping layers that are consecutive to one another in the axial direction of the examination volume. The slice thickness is selected as 3 mm, for example, so the displacement of the individual slices with respect to each other can be achieved with a spatially constant slice position such that the patient is moved at a specific speed on a patient bed in the axial direction. To record slice images from the various slices, a rapid gradient echo sequence, for instance FLASH, can be used, wherein ten images per second are recorded in this instance. The advance of the patient bed, in other words the patient bed increment, amounts here to 0.3 mm per slice image, which is shown more accurately in FIG. 2. The axial direction 1 with the extensions 2 of slices recorded consecutively is shown therein. Evidently the advance 3 of the patient bed amounts to precisely $\frac{1}{10}$ of the slice thickness indicated by the extension 2, so that after ten slices, in other words with the eleventh slice, the end of the first slice was reached, as indicated by the guide line 4.

If it is now assumed that the result, with pulsatile, fresh, unsaturated blood entering the slice to be scanned in the arterial phase, repeats every ten scans of a slice image at the latest, there should be at least one slice image that shows the result, in a group of ten consecutive slice images, for which the extensions 2 always lie within one slice thickness. The advance 3 is not selected arbitrarily, but instead precisely in view of the fact that when a duration of the cardiac cycle is assumed (here a predetermined maximum duration of 1000 ms), a cardiac cycle is also always assumed to have been completed within the advance by one slice thickness, which ensures the presence of a pulsatile influx of blood with a high signal intensity during the recording of at least one of the slice images within a group of ten slice images. The duration can be selected as a predetermined maximum duration, as shown, which in most cases proves expedient, but it is also possible to measure an actual, patient-specific duration and/or to determine the same from the slice images themselves, which will indicate a temporally regularly recurring stronger signal on account of the pulsatile inflow.

In a step S2, cf. FIG. 1 once again, the slice images are reconstructed in the spatial domain. To this end, any reconstruction method can be used. An iterative reconstruction method is preferably used.

Figure 2:
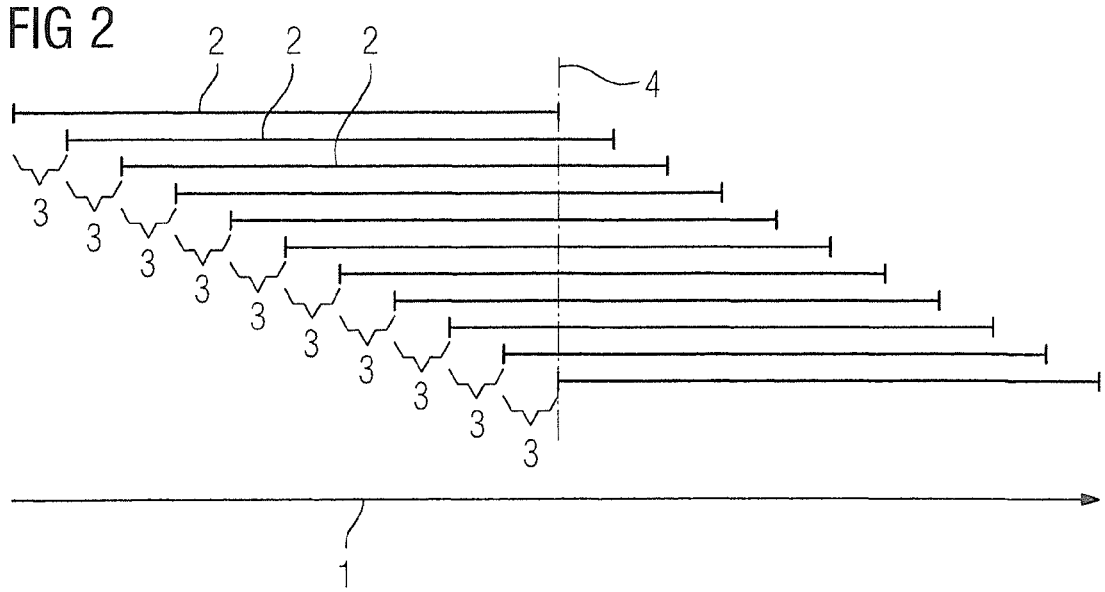
FIG. 2 is a block diagram of the sequence of slice images in the axial direction.

In a step S3, the slice images are then divided into groups of in each case two consecutively recorded slice images, which were consequently recorded in each case, cf. the explanation in FIG. 2 (a default duration of 1000 ms for a cardiac cycle, and starting point within a single slice thickness). For each of these consecutive groups, a maximum intensity projection image (MIP image) is determined in step S3 in a known manner by maximum intensity projection.

This maximum intensity projection image is used in the following step S4 as a reference image, in order to determine correlation measures of each slice image of the group for the corresponding maximum intensity projection image.

In a step S5, the slice image, among the images in a group that has the highest correlation measure to the maximum intensity projection image is then determined as a magnetic resonance angiograph image. The precise recording position for this slice image, which is now used as an angiography image, is naturally also known since it was recorded in step S1.

Such a slice image is consequently selected from each group so that, since each group sweeps over one slice image thickness, the angiography images are tight, but will only rarely follow one another with overlaps or at a distance. For instance, by adjusting the advance 3, less than one slice per cardiac cycle can be swept, in order to be able to determine tighter, and also more reliably overlapping, angiography images.

It should be noted again that the maximum intensity projection image can itself be used as an angiography image, wherein the recording position, at which the highest correlation measure is present, is then expediently assigned in an alternative step S5 to this maximum intensity projection image.

Figure 3:
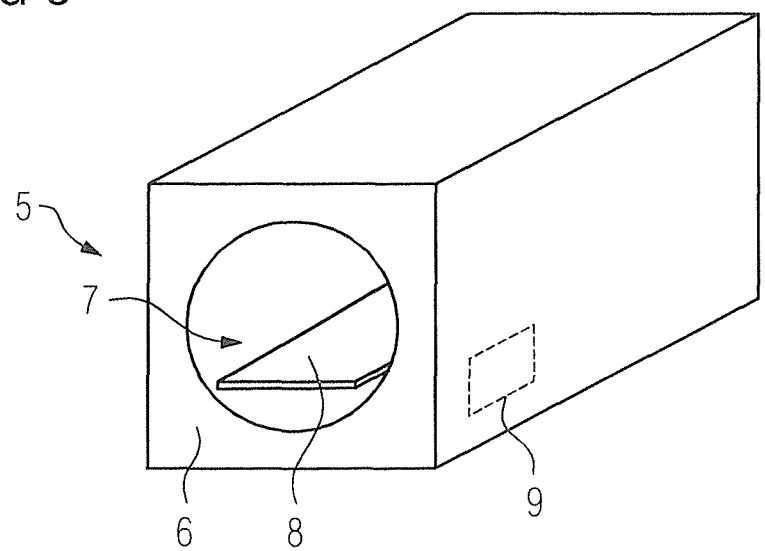
FIG. 3 schematically illustrates an inventive magnetic resonance device.

FIG. 3 is a block diagram of an inventive magnetic resonance apparatus 5. This has, as is fundamentally known, a scanner 6 with a patient receptacle 7, into which a patient can be introduced by a patient bed 8. The scanner 6 has a basic field magnet with gradient coil arrangement and a radio-frequency coil arrangement (not shown), which surround the patient receptacle 7. When the inventive method is implemented with the magnetic resonance apparatus 5, the patient bed 8 is used to move the patient during the recording of the slice images continuously through the spatially fixed slice, in which the recording takes place.

The operation of the magnetic resonance scanner 6 is controlled by a control computer 8, which is designed to perform the inventive method. To this end, the control computer 9 has a recording module, which actuates the remaining components of the magnetic resonance apparatus 5 in order to acquire the magnetic resonance data for the slice images. The recording module at the same time also controls the table advance. The slice images are determined in the spatial domain by a reconstruction module. A post-processing module for the division into groups, the maximum intensity projection and, based thereupon, the determination of the angiography images, in particular as the slice image with the best correlation measure, completes the modules of the control computer 9 provided to implement the inventive method.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating a magnetic resonance (MR) angiography image, comprising:

operating an MR scanner, while a patient is situated therein, to obtain a plurality of successive two-dimensional slice images that cover an examination volume of the patient along a direction slice-by-slice, using a time-of-flight angiography MR data acquisition sequence;

providing said plurality of slice images to a processor and, in said processor, dividing said plurality of slice images into respective groups with each group comprising a predetermined number of consecutive slice images along said direction;

in said processor, determining a maximum intensity projection image for each group using the slice images of that group; and in said processor, determining at least one diagnostic angiography image for each group by determining a correlation measure for each slice image in a respective group with regard to the maximum intensity projection image that was determined for that group, and thereby obtaining a plurality of correlation measures for each group, and determining said at least one diagnostic angiography image for the respective group dependent on an evaluation in said processor of the respective correlation measures for the slice images in that respective group and making the respective diagnostic angiography images for each group available in electronic form from said processor as respective data files.

2. A method as claimed in claim 1 comprising operating said MR scanner to acquire said plurality of two-dimensional slice images so that at least some successive slice images overlap each other.

3. A method as claimed in claim 1 comprising using a slice image that has the highest correlation measure in each group as the only diagnostic angiography image for that group.

4. A method as claimed in claim 1 comprising using all slice images in each group that have a correlation measure that exceeds a predetermined threshold value as diagnostic angiography images for that group.

5. A method as claimed in claim 1 comprising assigning a recording position to a slice image in each group having a highest correlation measure, and giving said at least one diagnostic angiography image for that group said recording position.

6. A method as claimed in claim 1 comprising determining said predetermined number as a function of an image recording rate of said plurality of two-dimensional slice images and as a function of a duration of the cardiac cycle of the patient.

7. A method as claimed in claim 6 comprising determining said predetermined number as a product of said duration and said image recording rate.

8. A method as claimed in claim 6 comprising using a predetermined maximum duration of said cardiac cycle as said duration.

9. A method as claimed in claim 8 comprising setting said predetermined maximum duration to be in a range between 800 and 1100 ms.

10. A method as claimed in claim 8 comprising setting said predetermined maximum duration to be 1000 ms.

11. A method as claimed in claim 6 comprising using a patient-specific duration of said cardiac cycle as said duration.

12. A method as claimed in claim 11 comprising determining said patient-specific duration of said cardiac cycle by evaluating said plurality of slice images in said processor.

13. A method as claimed in claim 1 comprising operating said MR scanner to acquire said plurality of two-dimensional slice images with respectively constant slice positions that are defined by a continuously moving patient table, on which said patient is situated, that moves through said MR scanner.

14. A method as claimed in claim 13 comprising selecting a movement speed of said patient table dependent on a slice thickness of one slice respectively represented by one of said plurality of two-dimensional slice images.

15. A magnetic resonance (MR) apparatus comprising:
an MR scanner;
a computer configured to operate said MR scanner, while a patient is situated therein, to obtain a plurality of successive two-dimensional slice images that cover an examination volume of the patient along a direction slice-by-slice, using a time-of-flight angiography MR data acquisition sequence;
said computer being configured to divide said plurality of slice images into respective groups with each group comprising a predetermined number of consecutive slice images along said direction;
said computer being configured to determine a maximum intensity projection image for each group using the slice images of that group; and
said computer being configured to determine at least one diagnostic angiography image for each group by determining a correlation measure for each slice image in a respective group with regard to the maximum intensity projection image that was determined for that group, and thereby obtaining a plurality of correlation measures for each group, and determining said at least one diagnostic angiography image for the respective group dependent on an evaluation in said computer of the respective correlation measures for the slice images in that respective group and to make the respective diagnostic angiography images for each group available in electronic form from said computer as respective data files.

16. A non-transitory, computer-readable data storage medium encoded with programming instructions, said storage medium being loaded into a control computer of a magnetic resonance (MR) apparatus that comprises an MR scanner, and
said programming instructions causing said control computer to:
operate said MR scanner, while a patient is situated therein, to obtain a plurality of successive two-dimensional slice images that cover an examination volume of the patient along a direction slice-by-slice, using a time-of-flight angiography MR data acquisition sequence;
divide said plurality of slice images into respective groups with each group comprising a predetermined number of consecutive slice images along said direction;
determine a maximum intensity projection image for each group using the slice images of that group; and
determine at least one diagnostic angiography image for each group by determining a correlation measure for each slice image in a respective group with regard to the maximum intensity projection image that was determined for that group, and thereby obtaining a plurality of correlation measures for each group, and determining said at least one diagnostic angiography image for the respective group dependent on an evaluation in said control computer of the respective correlation measures for the slice images in that respective group and make the respective diagnostic angiography images for each group available in electronic form from said control computer as respective data files.

17. A method as claimed in claim 1 comprising operating said MR scanner to obtain said plurality of successive two-dimensional slice mages along an axial direction of the patient, as said direction.

* * * * *